(12) United States Patent
Fagan

(10) Patent No.: US 10,195,683 B2
(45) Date of Patent: *Feb. 5, 2019

(54) METAL ANALYZING PLASMA CNC CUTTING MACHINE AND ASSOCIATED METHODS

(71) Applicant: Matthew Fagan, Middle Park (AU)

(72) Inventor: Matthew Fagan, Middle Park (AU)

(*) Notice: Subject to any disclaimer, the term of this patent is extended or adjusted under 35 U.S.C. 154(b) by 0 days.

This patent is subject to a terminal disclaimer.

(21) Appl. No.: 15/490,088

(22) Filed: Apr. 18, 2017

(65) Prior Publication Data

US 2017/0246703 A1 Aug. 31, 2017

Related U.S. Application Data

(60) Provisional application No. 62/421,919, filed on Nov. 14, 2016.

(51) Int. Cl.
*B23K 10/00* (2006.01)
*G01N 21/25* (2006.01)
*G01N 21/73* (2006.01)
*B23K 103/04* (2006.01)

(52) U.S. Cl.
CPC ........... *B23K 10/006* (2013.01); *G01N 21/73* (2013.01); *B23K 2103/04* (2018.08)

(58) Field of Classification Search
CPC ... B23K 10/006; B23K 2203/04; G01N 21/73
USPC .................................................... 219/121.44
See application file for complete search history.

(56) References Cited

U.S. PATENT DOCUMENTS

| | | | | |
|---|---|---|---|---|
| 3,451,666 A | * | 6/1969 | Evans | B23K 7/006 192/110 R |
| 4,532,219 A | * | 7/1985 | Hagen | G01N 31/12 250/288 |
| 4,641,968 A | * | 2/1987 | Grandy | G01N 21/67 315/209 CD |

(Continued)

FOREIGN PATENT DOCUMENTS

WO WO 2011/134805 11/2011

OTHER PUBLICATIONS

Australian Examination Report for Application No. 2017258847, dated Nov. 17, 2017, 10 pp.

(Continued)

*Primary Examiner* — Eric Stapleton
(74) *Attorney, Agent, or Firm* — Lathrop Gage LLP

(57) ABSTRACT

A plasma computer numerically controlled (CNC) cutting machine is controlled by a computer such as a personal computer capable running an operating system and software programs. In an embodiment, the computer executes a CNC program to control movement of a plasma torch to cut parts from a workpiece while a spectrometer determines an emissions spectra of light emitted as the torch cuts the workpiece. The spectrometer cooperates with software running on a computer to analyze the metal as it is being cut by the CNC cutting machine and determine a composition. In embodiments, the composition is compared to an expected composition and saved in a database with identifying information; in a particular embodiment the database is queried to provide identifying information of metal having similar composition to the workpiece.

2 Claims, 5 Drawing Sheets

(56) References Cited

U.S. PATENT DOCUMENTS

| | | | | |
|---|---|---|---|---|
| 4,689,754 A * | 8/1987 | Collins | G06Q 10/04 | 356/316 |
| 4,933,531 A * | 6/1990 | Ichikawa | B23K 11/31 | 219/86.25 |
| 4,983,807 A * | 1/1991 | Yamada | B23K 10/006 | 219/121.48 |
| 5,049,723 A * | 9/1991 | Macdonald | B23K 9/0956 | 219/121.67 |
| 5,085,499 A * | 2/1992 | Griffin | G01N 21/69 | 356/311 |
| 5,347,475 A * | 9/1994 | Taylor | G01J 3/02 | 356/326 |
| 5,464,958 A * | 11/1995 | Flowers | B23K 10/006 | 219/121.54 |
| 5,521,350 A * | 5/1996 | Nishi | B23K 9/0953 | 219/121.54 |
| 5,526,110 A * | 6/1996 | Braymen | G01N 21/73 | 250/252.1 |
| 5,571,478 A * | 11/1996 | Bartman | G01N 1/2258 | 422/94 |
| 5,614,110 A * | 3/1997 | Shintani | B23K 10/00 | 219/121.39 |
| 5,751,416 A * | 5/1998 | Singh | G01J 3/30 | 356/300 |
| 5,777,735 A * | 7/1998 | Reagen | G01J 3/453 | 356/244 |
| 5,814,784 A * | 9/1998 | Kinsman | B23K 26/032 | 219/121.6 |
| 5,866,871 A * | 2/1999 | Birx | H01J 27/04 | 219/121.48 |
| 5,874,708 A * | 2/1999 | Kinsman | B23K 26/034 | 219/121.64 |
| 5,889,587 A * | 3/1999 | D'Silva et al. | E21B 7/15 | 356/316 |
| 6,124,564 A * | 9/2000 | Sue | B23K 9/287 | 175/327 |
| 6,204,473 B1 * | 3/2001 | Legge | B23K 26/1476 | 219/121.67 |
| 6,274,841 B1 * | 8/2001 | Ramakrishnan | B23K 10/006 | 219/121.39 |
| 6,294,764 B1 * | 9/2001 | Lindner | F23G 5/085 | 110/250 |
| 6,374,158 B1 * | 4/2002 | Fusaro, Jr. | B23K 10/027 | 219/125.11 |
| 6,622,058 B1 * | 9/2003 | Picard | B23K 10/00 | 219/121.55 |
| 6,751,516 B1 * | 6/2004 | Richardson | B22F 3/1055 | 700/118 |
| 6,772,040 B1 * | 8/2004 | Picard | B23K 10/006 | 219/121.11 |
| 6,940,037 B1 * | 9/2005 | Kovacevic | B23K 9/044 | 219/121.45 |
| 6,947,802 B2 * | 9/2005 | Picard | B23K 10/00 | 219/121.39 |
| 6,995,334 B1 * | 2/2006 | Kovacevic | B23K 26/032 | 219/121.63 |
| 7,020,539 B1 * | 3/2006 | Kovacevic | B22F 3/1055 | 483/16 |
| 7,022,935 B1 * | 4/2006 | Matus | B23K 10/00 | 219/121.39 |
| 7,045,738 B1 * | 5/2006 | Kovacevic | B05B 7/144 | 219/121.63 |
| 7,092,784 B1 * | 8/2006 | Simkins | A61C 7/08 | 433/6 |
| 7,106,438 B2 * | 9/2006 | Morrisroe | G01N 21/73 | 250/288 |
| 7,123,361 B1 * | 10/2006 | Doughty | G01J 3/02 | 356/316 |
| 7,186,947 B2 * | 3/2007 | Connally | B23K 10/00 | 219/121.72 |
| 8,395,075 B2 * | 3/2013 | Phillip | B23K 10/00 | 219/121.44 |
| 8,541,710 B2 * | 9/2013 | Brandt | H05H 1/34 | 219/121.39 |
| 8,865,056 B2 * | 10/2014 | Fagan | B23K 37/0288 | 266/54 |
| 9,144,882 B2 * | 9/2015 | Lindsay | B23K 5/00 | |
| 9,395,715 B2 * | 7/2016 | Brandt | B23K 5/00 | |
| 9,481,050 B2 * | 11/2016 | Brine | B23K 10/00 | |
| 9,643,273 B2 * | 5/2017 | Adams | B23K 9/013 | |
| 9,649,715 B2 * | 5/2017 | Winn | B23K 10/006 | |
| 9,731,375 B2 * | 8/2017 | Friedel | B23K 10/00 | |
| 9,737,954 B2 * | 8/2017 | Hoffa | B23K 10/006 | |
| 9,743,672 B2 * | 8/2017 | Pierce | A01N 59/16 | |
| 2003/0204283 A1 * | 10/2003 | Picard | B23K 10/00 | 700/166 |
| 2004/0159643 A1 * | 8/2004 | Mutoh | B23K 26/046 | 219/121.83 |
| 2004/0169855 A1 * | 9/2004 | Morrisroe | G01N 21/73 | 356/316 |
| 2004/0188397 A1 * | 9/2004 | Connally | B23K 10/00 | 219/121.67 |
| 2005/0046825 A1 * | 3/2005 | Powell | G01N 21/73 | 356/72 |
| 2005/0173380 A1 * | 8/2005 | Carbone | B22F 3/1055 | 219/121.31 |
| 2005/0178749 A1 * | 8/2005 | Yamazaki | B23K 26/03 | 219/121.62 |
| 2006/0122055 A1 * | 6/2006 | Gaffney | B01J 23/002 | 502/208 |
| 2006/0274421 A1 * | 12/2006 | Okamitsu | A61C 13/001 | 359/618 |
| 2006/0274989 A1 * | 12/2006 | Gergely | C03B 19/1025 | 385/12 |
| 2006/0274990 A1 * | 12/2006 | Gergely | B82Y 5/00 | 385/12 |
| 2007/0221620 A1 * | 9/2007 | Sakthivel | G01N 21/73 | 216/59 |
| 2007/0247620 A1 * | 10/2007 | Koo | G01J 3/44 | 356/301 |
| 2008/0014653 A1 * | 1/2008 | Bloom | G01J 3/443 | 436/171 |
| 2008/0299543 A1 * | 12/2008 | Gailer | G01N 30/88 | 435/4 |
| 2008/0319375 A1 * | 12/2008 | Hardy | A61K 9/0009 | 604/22 |
| 2009/0240368 A1 * | 9/2009 | Young, Jr. | B23K 31/10 | 700/166 |
| 2010/0133247 A1 * | 6/2010 | Mazumder | B23K 9/02 | 219/121.83 |
| 2010/0187091 A1 * | 7/2010 | Pierce | B01J 19/088 | 204/164 |
| 2010/0284003 A1 * | 11/2010 | Hamilton | G01J 1/02 | 356/310 |
| 2011/0005940 A1 * | 1/2011 | Pierce | B22F 3/003 | 205/687 |
| 2011/0095198 A1 * | 4/2011 | Smiljanic | B22F 3/105 | 250/396 R |
| 2011/0152476 A1 * | 6/2011 | Gessner | C08F 6/02 | 526/68 |
| 2012/0044488 A1 * | 2/2012 | Senac | G01J 3/02 | 356/316 |
| 2012/0242015 A1 * | 9/2012 | Fagan | B23K 37/0288 | 266/59 |
| 2013/0062323 A1 * | 3/2013 | Hassan | G01N 21/718 | 219/121.62 |
| 2013/0259903 A1 * | 10/2013 | Mortenson | B22F 1/0022 | 424/400 |
| 2014/0072836 A1 * | 3/2014 | Mills | C25B 1/04 | 429/8 |
| 2014/0268132 A1 * | 9/2014 | Hamilton | G01J 3/0229 | 356/310 |
| 2015/0064278 A1 * | 3/2015 | Pierce | B01J 19/088 | 424/618 |
| 2015/0171455 A1 * | 6/2015 | Mills | H01M 8/144 | 429/422 |
| 2015/0269603 A1 * | 9/2015 | Young, Jr. | G06Q 30/0226 | 705/14.27 |

(56) References Cited

U.S. PATENT DOCUMENTS

| | | | | |
|---|---|---|---|---|
| 2015/0332071 A1* | 11/2015 | Hoffa | ............... | B23K 5/00 |
| | | | | 340/10.2 |
| 2015/0371129 A1* | 12/2015 | Hoffa | ............... | B23K 5/00 |
| | | | | 340/10.2 |
| 2016/0059363 A1* | 3/2016 | Ardisson | ............ | B23K 37/0288 |
| | | | | 219/121.39 |
| 2016/0109358 A1* | 4/2016 | Katz | ............... | G01J 3/443 |
| | | | | 356/402 |
| 2016/0151859 A1* | 6/2016 | Sparks | ............. | B23K 26/034 |
| | | | | 219/121.62 |
| 2016/0221108 A1* | 8/2016 | Hoffa | ............... | B23K 10/006 |
| 2017/0124360 A1* | 5/2017 | Young, Jr. | ........ | G06K 7/10009 |

OTHER PUBLICATIONS

International Search Report and Written Opinion of PCT/IB2017/055215, dated Nov. 21, 2017, 5 pp.

U.S. Appl. No. 15/886,806 Office Action dated Apr. 11, 2018, 24 pages.

\* cited by examiner

METAL ANALYZING PLASMA CNC CUTTING MACHINE AND ASSOCIATED METHODS

RELATED APPLICATIONS

This application claims priority to U.S. Patent Application Ser. No. 62/421,919, titled "Metal Analyzing Plasma NC Cutting Machine And Associated Methods", filed Nov. 14, 2016, and incorporated herein by reference.

FIELD OF THE INVENTION

This invention pertains to plasma metal cutting using a numerically controlled machine and spectral analysis to determine metallurgical composition of metal.

BACKGROUND

When purchasing steel from multiple sources, quality of the steel may not be as dependable and as stable as when purchasing steel from a single source. Also, some steel has unusual composition such as alloying components like Boron, which reduces import duty but affects the behavior of the metal and requires different welding. When this chemical composition becomes hidden in the steel supply chain, the steel can be dangerous.

Originally, only chemical analysis could determine metallurgical components of the steel, and specialty steel suppliers employed metallurgists with laboratory equipment to test the steel. With the rapid availability of high performance microcomputers, heavy stand-alone machines use an arc for spectrographic analysis of a metal sample. Newer test equipment uses Energy Dispersive X-ray Fluorescence (ED-XRF) technology for spectral analysis of steel, although they are expensive and not practical for steel processing workshops.

Plasma cutters have become common for metalworking, including working with steel, aluminum, and other metals. In plasma cutting, a plasma formed of a gas heated by an electric arc serves to conduct electricity into, and remove melted metal from, a metal workpiece. Plasma cutters may be used with "numerically controlled" (NC), computer controlled cutting machines, or may be handheld.

SUMMARY

A plasma computer numerically controlled (CNC) cutting machine is controlled by a computer such as a personal computer capable running an operating system and software programs. In an embodiment, the computer executes a CNC program to control movement of a plasma torch to cut parts from a workpiece while a spectrometer determines an emissions spectra of light emitted as the torch cuts the workpiece. The spectrometer cooperates with software running on a computer to analyze the metal as it is being cut by the CNC cutting machine and determine a composition. In embodiments, the composition is compared to an expected composition and saved in a database with identifying information; in a particular embodiment the database is queried to provide identifying information of metal having similar composition to the workpiece In an embodiment, a method for analyzing composition of a workpiece being cut by a plasma CNC cutting machine, includes capturing light from a plasma arc of the plasma CNC cutting machine as the plasma arc cuts a part from the workpiece; generating spectral data from the light; and processing the spectral data to generate a determined composition indicative of composition of the workpiece.

In another embodiment, a plasma CNC cutting machine of the type having a bed for supporting a workpiece to be cut, a gantry that traverses the bed, a plasma cutting head apparatus mounted to the gantry, and a computer having a processor and memory storing CNC control software having instructions executable by the processor to control the gantry and the plasma cutting head apparatus to cut the workpiece with a plasma arc, has improvements including a lens positioned and configured to capture light from the plasma arc and direct the light through an optical path; a spectrometer configured to analyze light received through the optical path and generate spectral data therefrom; and spectral analysis software comprising machine readable instructions stored in the memory and executable by the processor to analyze the spectral data and generate a determined composition indicative of composition of the workpiece.

In yet another embodiment, a metal analyzing plasma CNC cutting machine, includes a plasma cutting torch controllable to cut a workpiece with a plasma arc; a lens positioned and configured to capture light from the plasma arc; a spectrometer coupled to receive light from the lens through an optical fiber path and adapted to determine spectral data of the light; at least one computer having a processor and memory storing spectral analysis software that includes machine readable instructions executable by the processor to analyze the spectral data and generate a determined composition indicative of a composition of the workpiece.

DETAILED DESCRIPTION OF THE EMBODIMENTS

Figure 1:
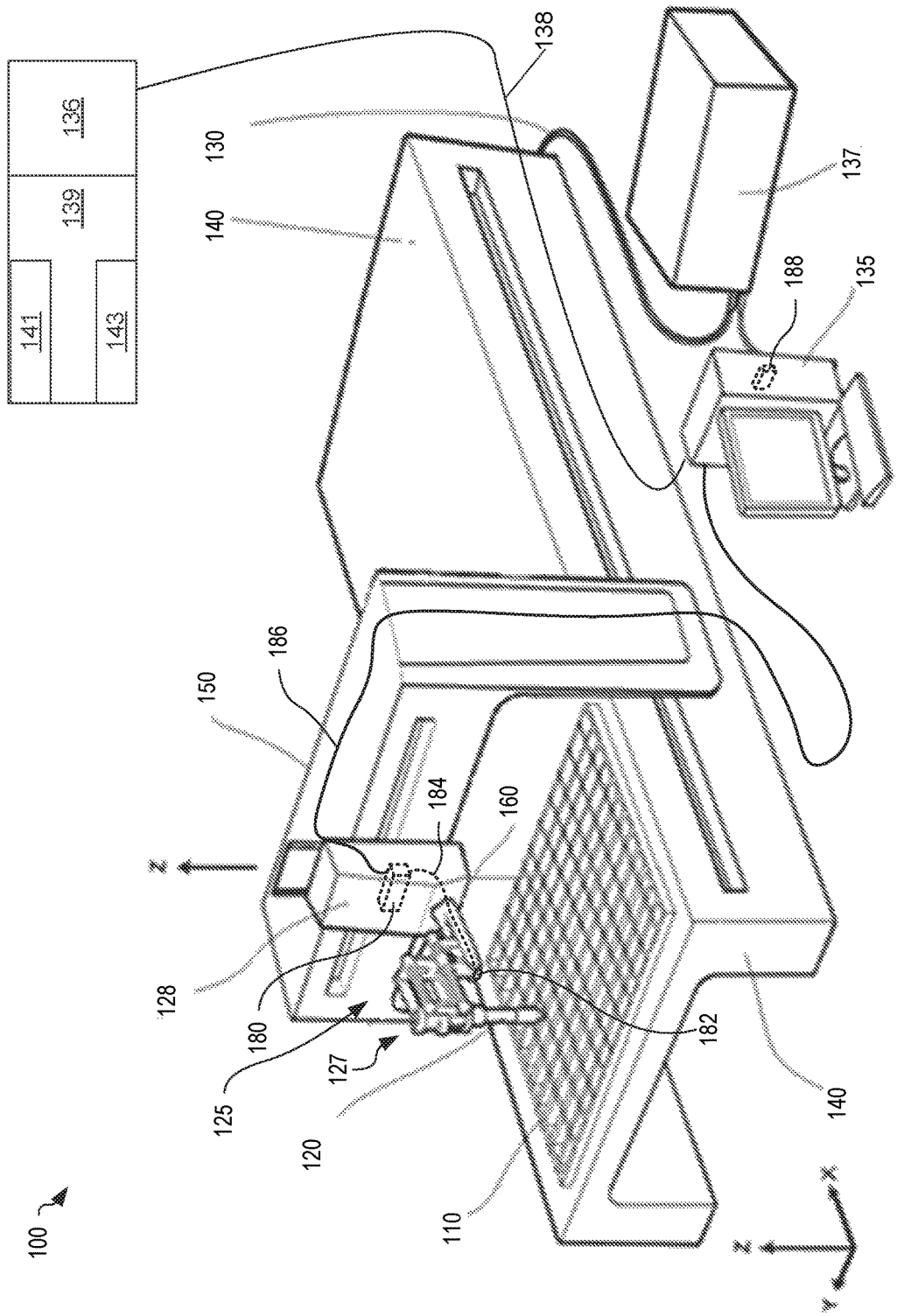
FIG. 1 shows one example of a metal analyzing plasma CNC cutting machine, in an embodiment.

FIG. 1 shows an example metal analyzing plasma CNC cutting machine 100. Similar to conventional plasma cutting machines, machine 100 includes a bed 140, a gantry 150, and a head apparatus 125 that holds and manipulates a plasma torch 120. A computer 135 (e.g., a personal computer capable running an operating system and software programs) communicates with a remote amplifier box 137 that generates signals through cable 130 for controlling servo motors of gantry 150, head apparatus 125, and plasma torch 120. A metallic workpiece 110 to be cut by machine 100 is placed on bed 140. In the example of FIG. 1, workpiece 110 is a steel grating but may represent any metallic material that may be cut by machine 100 such as steel, aluminum, or brass sheet or plate up to six inches thick.

In certain embodiments, head apparatus 125 may be a bevel head apparatus such as can be found in U.S. Pat. No. 8,865,056, which is included herein by reference for purpose of enablement. Bevel head apparatus 125 holds, swivels and tilts torch 120 up to 57 degrees in any plane. Bevel head apparatus 125 includes a pantograph arm 127 that is mounted to an actuator box 128 that contains motors and drivers that manipulate the pantograph arm and plasma torch 120 to cut workpiece 110. Actuator box 128 is formed of metal and acts as a 'Faraday cage' to shield electronics included therein from radiation and heat generated by the plasma arc. Box 128 may be cooled in some embodiments, such as by fans.

In a particular embodiment, plasma torch 120 is initiated by 5,000 volts at a frequency of 2 MHz that ionizes gas released in a high pressure stream to form a plasma arc with a temperature of around 10,000 C. This plasma arc draws a DC current of between 10 amps and 1200 amps at around 150 volts once established. The power released by the plasma arc may reach 180 kW and is typically around 37 kW, and is sufficient to melt thick steel quickly using only electricity and air (although other gas mixes may be used). The plasma arc and melting steel is hot and emits light that carries a wealth of spectral information about the steel being cut, particularly in the electromagnetic spectrum range of Ultra Violet (UV) light.

The plasma arc creates a difficult environment for electronic devices, as it is very hot, splatters molten metal, and its arc-formation power supply of 5,000 volts at a frequency of 2 MHz, generates considerable electromagnetic radiation that interferes with nearby electronic devices. It is therefore difficult to position sensitive electronic equipment near plasma torch 120.

A fiber optic cable allows the sensing electronics to be safely isolated inside a metal Faraday cage while continuously collecting light from the plasma arc. The Faraday cage shields the sensing electronics from the electromagnetic radiation (radio interference) and heat generated by the plasma arc.

Thus, by combining the spectral analyzer, coupled by the fiber optic to the plasma CNC cutting machine, emissions spectra from the metallurgic components of the steel being cut may be monitored periodically or continuously, and those emissions spectra analyzed to determine metallurgic components of the steel being cut. This analysis is similar to the analysis done for spark analysis which also uses an electric arc to generate light to determine a composition of a metal sample. However, the advantages of machine 100 include that the analysis takes no additional time or effort beyond that needed to cut the workpiece 110.

Pantograph arm 127 is modified to include a lens 182, positioned to capture electromagnetic radiation, particularly in the ultraviolet light portion of the spectrum, from the plasma arc formed by plasma torch 120 while the plasma arc is cutting workpiece 110. For example, lens 182 has a focal length based upon its position relative to the plasma arc, to capture light (i.e., at least a portion of the electromagnetic spectrum) generated by the plasma arc. An optical path 184, which may be a single strand or a multiple-strand fiber optic cable, optically couples lens 182 to a spectrometer 180 positioned within box 128. Thus, spectrometer 180 is protected from interference from the plasma arc but receives light emitted from the plasma arc, via lens 182 and optical path 184, while cutting workpiece 110. Spectrometer 180 is selected based upon the spectral ranges of light produced by the plasma arc of the cutting torch as known in the art of spectral analysis. In one example, spectrometer 180 is a Blue-Wave Miniature Fiber Optic Spectrometer device from StellarNet Inc., however, other spectrometer devices may be used without departing from the scope hereof.

Spectrometer 180 is communicatively coupled to computer 135 via a communication cable 186, such as an electrically screened cable or a fiber-optic communications cable. Spectrometer 180 may share a communication path between bevel head apparatus 125 and computer 135 without departing from the scope hereof. In one particular embodiment, communication cable 186 is a USB cable. Computer 135 includes software 188 that processes data received from spectrometer 180 to determine metallurgical content of workpiece 110 based upon a spectrum captured by spectrometer 180 while workpiece 110 is being cut by machine 100.

Figure 2:
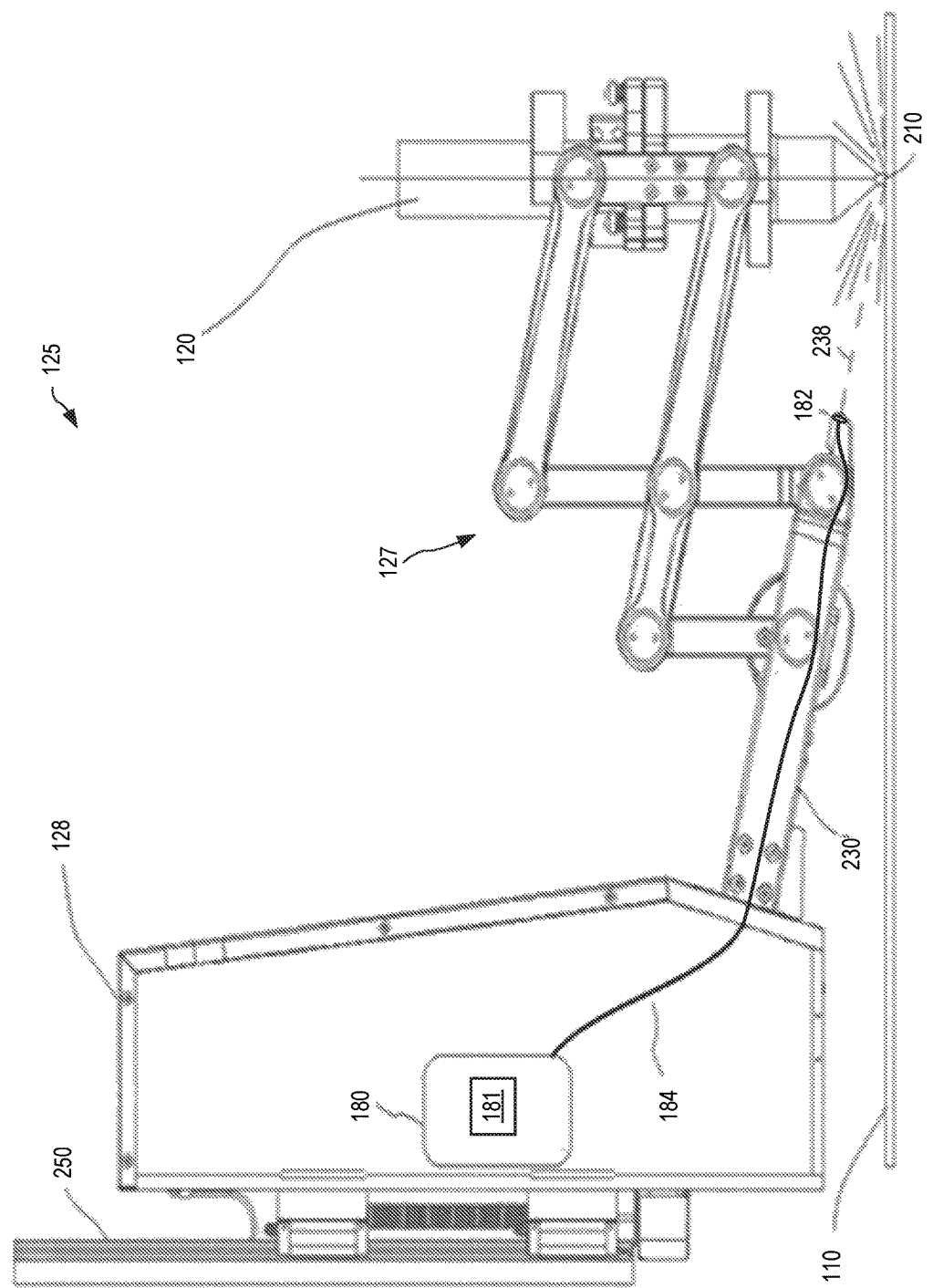
FIG. 2 shows the bevel head of the plasma CNC cutting machine of FIG. 1 in further detail showing a spectral analyzer optically coupled to a lens positioned proximate plasma arc, in an embodiment.

FIG. 2 shows bevel head apparatus 125 of metal analyzing plasma CNC cutting machine 100 of FIG. 1 in further exemplary detail. Lens 182 is positioned on a lower armature 230 of pantograph arm 127 in alignment 238 with a plasma arc 210 formed by plasma torch 120. As such, the position of lens 182 relative to the plasma arc 210 is constant, since, due to the advantages of the pantograph design, the center of plasma arc 210 does not move relative to lower armature 230. Further, as plasma torch 120 is moved to cut workpiece 110, lens 182 remains in a constant position relative to plasma arc 210. That is, lens 182 is positioned on the arm supporting plasma torch 120 and moves with the torch. When other forms of cutting head are used instead of bevel head apparatus 125, lens 182 is similarly positioned to ensure that lens 182 is aligned with plasma arc 210, and remains in close proximity to the plasma arc to capture light from the plasma arc while excluding most surrounding ambient light, and moves as the plasma arc moves to cut workpiece 110. For example, as bevel head apparatus 125 moves up and down relative to a backplane 250, which in turn moves left and right relative to gantry 150, which in turn moves backwards and forwards relative to bed 140, lens 182 remains aligned with, and in close proximity to, plasma arc 210.

Optical path 184 conveys the light captured by lens 182 to spectrometer 180 that spectrally analyzes the light to generate spectral data 181. Spectral data 181 is for example a digital representation of spectral content of the light captured by lens 182 from plasma arc 210. Lens 182 moves together with bevel head apparatus 125 as torch 120 is controlled to cut workpiece 110 and spectrometer 180 is positioned a safe distance from plasma arc 210 and couples via optical path 184.

As shown in FIG. 2, lens 182 is positioned at a distal end of lower armature 230 to capture at least part of the electromagnetic spectrum generated by plasma arc 210 as it cuts workpiece 110. Lens 182 may include a front element or window that is replaceable in the event of damage caused by plasma arc 210 or splattered molten metal. Optical path 184 may be positioned within lower armature 230 for protection from damage by plasma arc 210 and is for example a flexible fiber optical cable that conveys light from lens 182 to spectrometer 180. In an alternative embodiment, optical path 184 lies within a tubular conduit to protect it from damage. Spectrometer 180 is for example a micro spectrometer that uses a diffraction grating and sensing array to derive spectral data 181 from the light received via optical path 184, the spectral data includes an intensity and wavelength (or equivalently frequency) distribution of light generated by plasma arc 210. Spectral data 181 is sent to computer 135 for further analysis.

Figure 3:
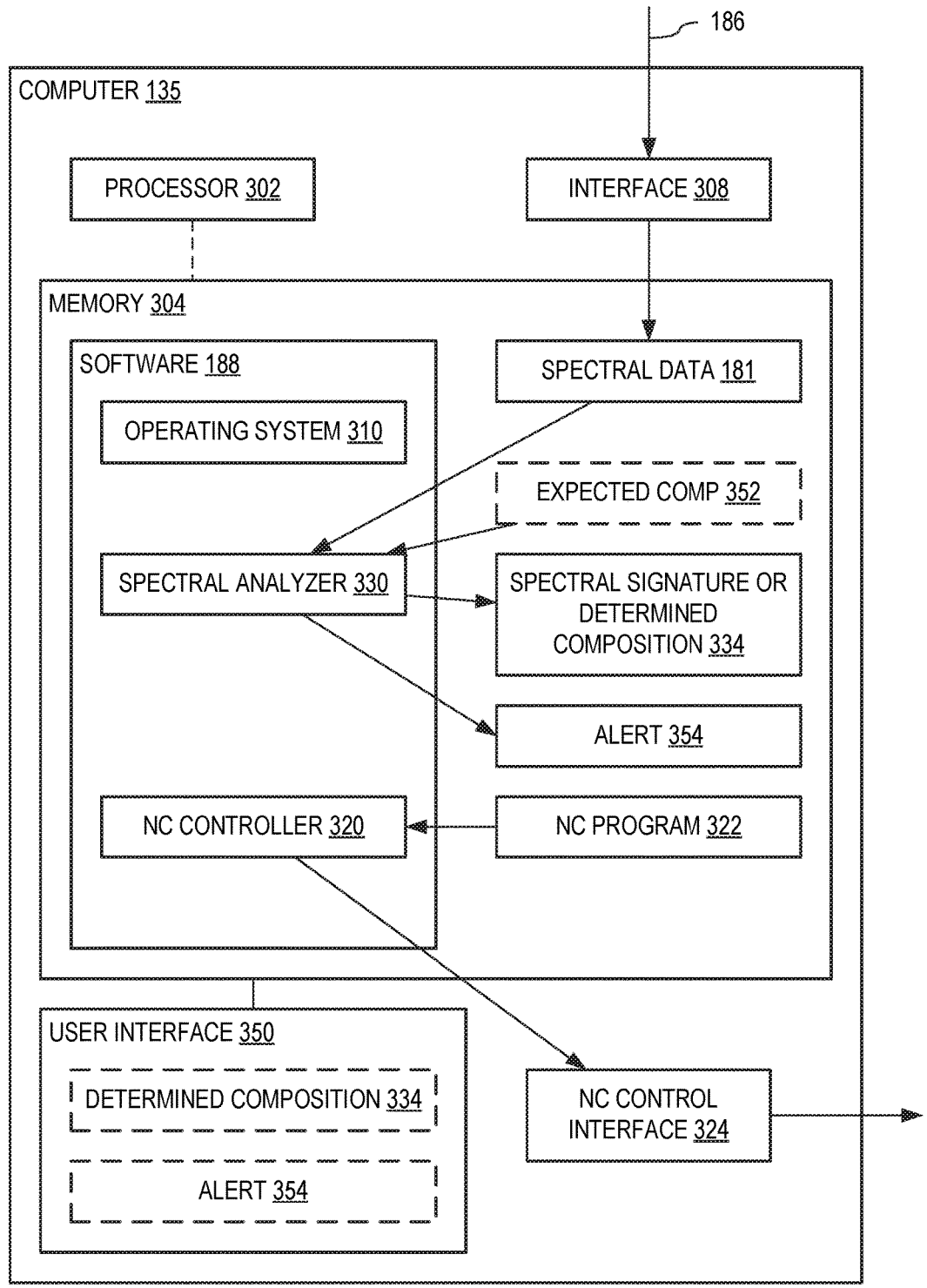
FIG. 3 shows the computer of FIG. 1 in further example detail, in an embodiment.

FIG. 3 shows computer 135 in further example detail. Computer 135 includes at least one processor 302 communicatively coupled to memory 304. Memory 304 is non-transitory and represents one or both of volatile memory (e.g., RAM, SRAM, DRAM, and so on) and nonvolatile memory (e.g., ROM, PROM, EPROM, FLASH, magnetic media and optical media). Memory 304 is shown storing software 188 that includes an operating system 310, a CNC controller 320 function, and a spectral analyzer 330 routine. Operating system 310 provides a real-time multitasking environment within computer 135 for concurrently executing CNC controller 320 and spectral analyzer 330. Operating system 310 is selected from the group including Microsoft® Windows™, Apple® OS™, and so on. For example, operating system 310 coordinates execution of CNC controller 320 and spectral analyzer 330.

CNC controller 320 follows a CNC program 322 to control movement and operation of plasma torch 120 to cut parts from workpiece 110 as desired. For example, CNC controller 320 may send commands, via CNC control interface 324 and remote amplifier box 137, to each of gantry 150, bevel head apparatus 125 and plasma torch 120. As known in the art of CNC controllers, CNC controller 320, gantry 150, and bed 140 are configured so that CNC controller 320 can direct movement of gantry 150 along bed 140, and of bevel head apparatus 125 along gantry 150, thereby permitting CNC controller 320 to move bevel head apparatus 125 to position plasma torch 120 at any X-Y coordinate in a predefined operational area lying within a plane over and parallel to bed 140. Similarly, CNC controller 320 is configured to control motors within box 128 to operate pantograph arm 127 to position plasma torch 120 at any Z or height coordinate within a predefined operational volume incorporating the plane over and parallel to bed 140. CNC controller is thereby configured to position torch 120 at any position within the predefined operational volume as needed to make preprogrammed cuts to workpiece 110.

Operating system 310 runs spectral analyzer 330 concurrently with CNC controller 320 to process spectral data 181, received via interface 308 and communication cable 186 from spectrometer 180, and generate determined composition 334. CNC controller 320 and spectral analyzer 330 may communicate such that spectral analyzer 330 controls spectrometer 180 to capture spectral data 181 only when plasma torch 120 is active and plasma arc 210 is present.

In one example of operation, CNC controller 320 and spectral analyzer 330 cooperate to capture spectral data 181, the spectral data including emissions spectra information, from different areas of cut of workpiece 110 as it is cut by machine 100, and spectral analyzer 330 generates determined compositions 334 for each different area of cut.

For purposes of this document, a composition of a metal workpiece, such as workpiece 110, is a list of elements that may be found in metal workpieces together with a percentage of each element of the list that is present in the workpiece. For example metal workpieces of cast iron, steel, aluminum, brass, bronze, or copper may contain aluminum, arsenic, beryllium, bismuth, boron, carbon, cerium, chromium, copper, iron, lead, magnesium, manganese, molybdenum, nickel, phosphorous, silicon, silver, sulfur, tin, titanium, tungsten, vanadium, zinc, and zirconium at various percentages. It is well known that percentages of each element present in a metal workpiece may dramatically affect physical properties such as hardness of the workpiece, as well as chemical properties like corrosion resistance, for example hardness of steel is significantly affected by carbon percentage content, and corrosion resistance by chromium, and nickel percentage content. Similarly, copper-based alloys have physical properties that are significantly affected by tin, zinc, and aluminum percentages. Generally, emissions spectra of each element in isolation are known. Emissions spectral data 181 includes a superposition of emissions spectra of the elements included in a composition of workpiece 110.

Various bodies, including the Society of Automotive Engineers (SAE) and ASTM International, have published named specifications for metal, such as SAE grade 440 steel, ASTM A1 for railroad rails, ASTM A182 for stainless steel pipe fittings, A354 for steel alloy bolts, and A514 for weldable steel plate; each specification includes a range of allowable percentages of specific elements for composition of metal acceptable under the specification as well as other factors, such as heat treatments, used in producing metal objects to meet the specification. Other specifications, such as for rifle barrels, armor plate and bolts, screws, and sheetmetal used in aircraft construction, have been published by governmental and military agencies. These specifications may be referenced by those who order metal from foundries.

In each specification, some elements are regarded as desired, mandatory, alloy constituents, such as iron and carbon in steel, typically added intentionally when workpieces are made at a foundry and for which associated percentages appear in specifications as ranges with non-zero minimum and maximum values. Other elements, such as excessive boron or sulfur in steel, may be regarded as objectionable impurities, with only a maximum listed for some specifications, but are sometimes present in workpieces. Still other elements, such as rare earth elements or actinide series elements, may be present in trace amounts, their percentages in composition of workpieces is useful in fingerprinting workpieces even though they may not be listed in common specifications and may be at sufficiently low concentrations that they do not significantly alter material properties of the workpiece.

Spectral analyzer 330 includes include machine readable instructions that, when executed, perform methods known in the art for identifying peaks in spectral data 181 and fit known emissions spectra of each element of a composition of workpiece 110 to observed emissions spectra, thereby identifying percentages of each element in workpiece 110 and determining determined composition 334 of workpiece 110. While percentages of most elements in workpiece 110 can be identified using air as the gas from which the plasma is formed, in some embodiments an inert gas such as argon is used as the supplied gas so that percentages of oxygen and nitrogen in the workpiece 110 can be determined during cutting.

In some embodiments, an expected composition 352 of workpiece 110 is defined prior to cutting of workpiece 110. In embodiments, expected composition 352 includes ranges of acceptable content for particular elements. In a particular embodiment, this desired composition is entered into computer 135 as expected composition 352. In an alternative embodiment, a specification identifier is entered into computer 135, whereupon computer 135 queries a database 139 on a server 136, which returns expected composition ranges from a specification entry 141 of database 139 to computer 135 as expected composition 352. In either embodiment, once cutting of workpiece 110 by machine 100 starts, spectral analyzer 330 determines determined composition 334 from light of plasma arc 210, and compares the determined composition 334 to expected composition 352, generating an alert 354 when determined composition 334 indicates that workpiece 110 is not of the expected composition 352. For example, spectral analyzer 330 and computer 135 may be configured to ignore variations in composition that are within limits of a specification or to ignore other minor variations in composition, and/or may be configured to generate alert 354 when unwanted contaminants are identified in workpiece 110 or determined composition lies outside limits of a specific specification.

Computer 135 may also include a user interface 350 for interacting with an operator of machine 100, and user interface 350 may display one or both of determined composition 334 and alerts 354 to the operator as machine 100 cuts workpiece 110.

In an embodiment, computer 135 is coupled through a computer network 138, which in a particular embodiment is a local network and in another particular embodiment is the Internet, to server 136 having steel composition information in database 139.

In embodiments having database 139, database 139 may be configured with specification entries 141 for each of several specifications of metal, such as steel, with composition ranges for each specification. In a particular embodiment, database 139 is configured with a table of acceptable compositions, typically entered as ranges of percentages for each of several elements, indexed by published specification identifiers.

In embodiments having database 139, database 139 may also be configured with composition database entries 143 having determined compositions, or fingerprints, for metal of each of several specifications as produced by each of several foundries. These determined compositions may be measured by plasma cutting machines herein described, or determined by spectrometric analysis with other equipment. In embodiments having composition database entries 143, computer 135 is configured to upload a determined composition 334 of each workpiece 110 to database 139 as an additional composition database entry 143 with any identified specification and identification of the foundry or steel mill the workpiece originated from.

It is known that iron ore varies in composition from mine to mine, and that impurities found in ore may appear in smelted metal. For example, iron ore from the Dannemora mine in Sweden was low in phosphorus and sulfur, while high in certain other metals; during the seventeenth and eighteenth centuries cast iron cannon made from Dannemora ore developed a reputation as being much less likely to explode when fired than cannon made from iron ore from many other sources because of the ore's low sulfur and phosphorous content. While major impurities and amounts of alloying elements, including sulfur and phosphorous, are often corrected during modern smelting and foundry operations, other, minor, alloying elements and impurities may not be corrected and will show as minor elements in determined composition 334. Typically, major impurities and alloying elements are associated with a specification of metal in workpiece 11, while minor elements in workpiece 110 are associated with a source from which the workpiece originated. The pattern of these impurities in determined compositions in database 139 can therefore serve to help identify a source for the workpiece.

In an embodiment, after determining determined composition 334, computer 135 and server 136 are configured to search database 139 for composition database entries 143 most closely matching in major alloying elements to determined composition 334 and provide identifying information to a user regarding specifications associated with those nearest composition entries. Further, computer 135 and server 136 are configured to search database 139 for composition database entries 143 most closely matching in minor elements to determined composition 334 and provide a fingerprint identifying information to a user regarding a likely source of metal in workpiece 110. For example, for a stainless steel workpiece, iron, nickel and chromium are major alloying elements added with percentages greater than one percent during foundry operations and are indicative of a specification for the stainless steel, while certain other elements of determined composition 334 are typically not intentionally added and their concentrations are part of the fingerprint for identifying a source of the metal in workpiece 110.

Figure 4:
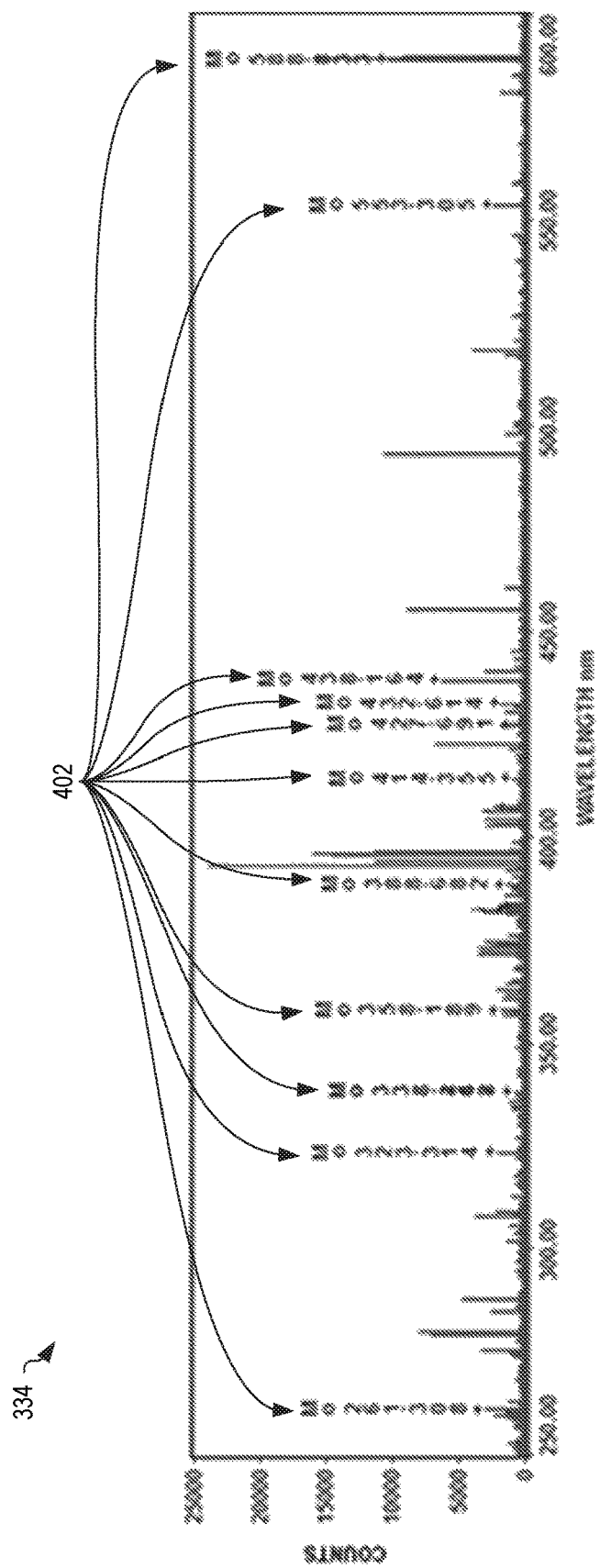
FIG. 4 is a spectral graph illustrating example spectral data captured by the metal analyzing plasma CNC cutting machine of FIG. 1 when cutting the workpiece, in an embodiment.

FIG. 4 shows one example spectral data 181 captured by metal analyzing plasma CNC cutting machine 100 of FIG. 1 when cutting workpiece 110. In this example, workpiece 110 is stainless steel and contains molybdenum and spectral data 181 shows a plurality of spectral features 402 that correspond to the presence of molybdenum in steel. Determined composition 334 may be generated from spectral data 181 near instantly as spectral data 181 is sent to computer 135 as machine 100 cuts workpiece 110. Determined composition 334 shows the constituent elements of workpiece 110 in proportion. For steel, a major constituent is Iron (Fe), but it may include other constituents such as Chromium for stainless, Carbon, Molybdenum, Vanadium, Titanium, and Boron, and may also include impurities such as Sulfur and other elements. By providing machine 100 with simultaneous cutting and spectral analysis capability, the operator may verify that workpiece 110 is of correct composition and is warned of unwanted impurities or unexpected presence of critical alloying elements such as Boron. Being aware of unexpected composition at the first cut of workpiece 110 saves potentially wasted time in cutting and attempting to weld steel contaminated with Boron, for example. Spectral analysis of each workpiece also prevents unexpected reduction in finished item quality.

Figure 5:
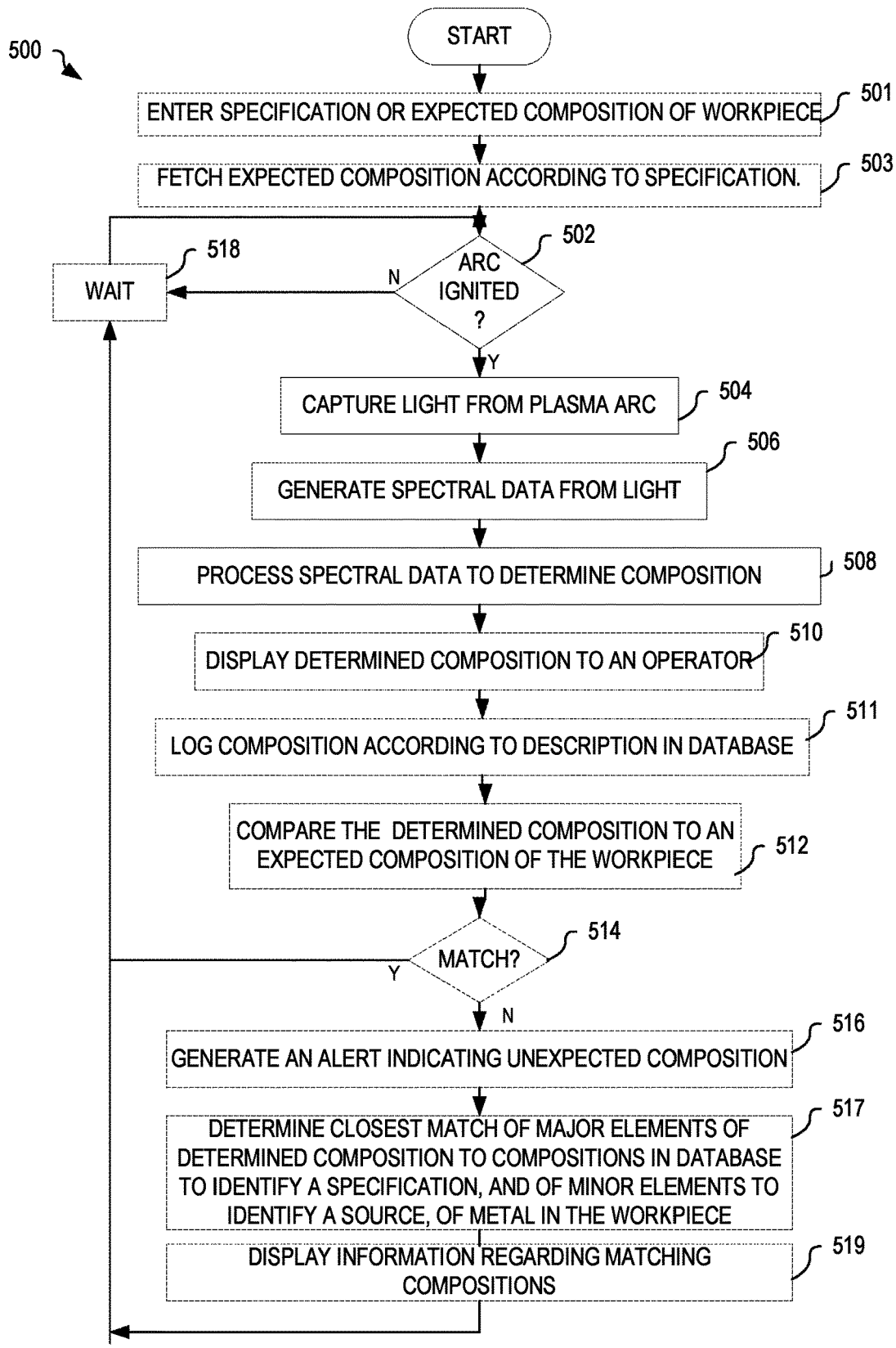
FIG. 5 is a flowchart illustrating one example method for analyzing metal using the metal analyzing plasma CNC cutting machine of FIG. 1, in an embodiment.

FIG. 5 is a flowchart illustrating one example method 500 for analyzing metal using metal analyzing plasma CNC cutting machine 100 of FIG. 1. Method 500 is implemented by lens 182, optical path 184, spectrometer 180, and computer 135 of machine 100. In this example, method 500 starts when machine 100 is about to cut, or has started cutting workpiece 110. If not already entered, a specification or desired composition of material of the workpiece is optionally entered 501 into computer 135. If a specification name is entered, in step 503, computer 135 is configured to access a corresponding specification entry 141 in database 139 of server 136 and fetch an expected composition database entry 143 from database 139 into local expected composition 352.

Step 502 is a decision. If, in step 502, method 500 determines that the arc has been ignited, method 500 continues with step 504; otherwise, method 500 continues with step 518. In one example of step 502, spectral analyzer 330 cooperates with CNC controller 320 to determine whether plasma arc 210 is operating on plasma torch 120. In another example of step 502, spectral analyzer 330 processes spectral data 181 to determine when plasma arc 210 is operating.

In step 504, method 500 captures light from the plasma arc. In one example of step 504, lens 182 captures light from plasma arc 210 and optical path 184 conveys the light to spectrometer 180. In step 506, method 500 generates spectral data from the light. In one example of step 506, spectrometer 180 generates, using a diffraction grating and sensors, spectral data 181 from light captured by lens 182.

In step 508, method 500 processes the spectral data and generates a determined composition. In one example of step 508, spectral analyzer 330 is executed by processor 302 to process spectral data 181 and generate determined composition 334.

Step 510 is optional. If included, in step 510, method 500 displays the determined composition of step 508 to an operator. In one example of step 510, spectral analyzer 330 displays determined composition 334 on user interface 350 of computer 135.

Step 511 is optional. If included, in step 511, method 500 logs the determined composition as an entry in the database. In one example of step 511, spectral analyzer 330 logs determined composition 334 as specification entry 141 of database 139.

Steps 512 through 516 are also collectively optional. If included, in step 512, method 500 compares the determined composition 334 to an expected composition 352 of the workpiece. Step 514 is a decision. If, in step 514, method 500 determines that the determined composition and the expected composition match to within limits, method 500 continues with step 518; otherwise, method 500 continues with step 516.

In step 516, method 500 generates an alert indicating unexpected composition. In one example of step 516, spectral analyzer 330 generates alert 354 and displays alert 354 on user interface 350. Method 500 then continues with step 517.

Steps 517 and 519 are optional. In step 517, method 500 inspects composition database entries 143 to determine a closest match of the determined composition 334 to determined composition portions of pre-existing database entries, first for major constituents to identify a specification of metal in the workpiece, and second for minor constituents to identify a source mill or foundry from which the metal originated. Then, in step 519, method 500 displays information, such as a SAE or ASTM specification name, and/or a foundry name, regarding the database entries that have the closest matches to the determined composition 334.

Step 518 is optional. If included, in step 518, method 500 waits. In one example of step 518, the wait is the predefined delay before repeating step 502. In another example of step 518, the wait is until plasma torch 120 moves to cut a different area of workpiece 110. Method 500 then continues with step 502. Steps 502 through 518 thus repeat to determine composition of workpiece 110 using spectral analysis as workpiece 110 is cut by plasma arc 210.

By combining spectral analysis and plasma CNC cutting in a single machine (i.e., metal analyzing plasma CNC cutting machine 100), one or more of the following advantages are achieved:

Spectral data is captured from the plasma arc as it cuts the workpiece, thereby avoiding the need for creating a separate arc or to use a laser to capture spectral data. This also avoids additional damage to the workpiece as would be needed for a separate test.

The optical fiber path allows the spectral capture device to be positioned away from the plasma arc to reduce interference.

Where the CNC cutting machine uses a bevel head apparatus, the actuator box is available to protect the spectral capture device—no additional protective enclosure is needed.

In embodiments, the available processing power of the computer used for executing the CNC program and controlling the cutting machine is also used to analyze the spectral data and generate the determined composition.

The combined solution makes valuable and often essential spectral analysis readily available, practical, and convenient for each cutting operation.

The combined solution is more cost effective than using separate spectral analyzing devices.

Automatic composition checks for each workpiece may be performed and the operator notified if the workpiece is of incorrect composition.

The combined solution provides information to control quality and prevent wrong materials from being used or supplied in a field where two quite different types of steel can look identical in a steel workshop.

Changes may be made in the above methods and systems without departing from the scope hereof. For example, although machine 100 is illustrated with a bevel head apparatus 125, other configurations for holding and manipulating torch 120 may be used. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A metal analyzing plasma CNC cutting machine, comprising:
   a plasma cutting torch controllable to cut a workpiece with a plasma arc;
   a lens positioned and configured to capture light from the plasma arc;
   a spectrometer coupled to receive the captured light from the lens through an optical fiber path and adapted to determine spectral data of the light;
   at least one computer having a processor and memory storing spectral analysis software that includes machine readable instructions executable by the processor to analyze the spectral data and generate a determined composition indicative of a composition of the workpiece,
   the spectral analysis software further comprising machine readable instructions stored in the memory and executable by the processor to compare the determined composition to an expected composition of the workpiece and to generate an alert on a user interface of the at least one computer when the determined composition does not match the expected composition.

2. The metal analyzing plasma CNC cutting machine of claim 1 wherein the spectral analysis software further comprises machine readable instructions configured to save the determined composition to a database on a server, and, when the expected composition of the workpiece does not match the determined composition, to identify a previous entry of the database having a closest match to the determined composition.

* * * * *